United States Patent
Bathen et al.

(10) Patent No.: US 8,366,440 B2
(45) Date of Patent: Feb. 5, 2013

(54) ROTATING ORTHODONTIC BRACKET WITH LOCKING MECHANISM

(75) Inventors: Juergen Bathen, McMinnville, OR (US); Rolf Hagelganz, Dundee, OR (US)

(73) Assignee: World Class Technology Corporation, McMinnville, OR (US)

( * ) Notice: Subject to any disclaimer, the term of this patent is extended or adjusted under 35 U.S.C. 154(b) by 0 days.

(21) Appl. No.: 13/463,722

(22) Filed: May 3, 2012

(65) Prior Publication Data
US 2012/0276496 A1 Nov. 1, 2012

Related U.S. Application Data

(63) Continuation-in-part of application No. 13/342,582, filed on Jan. 3, 2012, which is a continuation-in-part of application No. 12/807,859, filed on Sep. 14, 2010, now Pat. No. 8,113,828.

(51) Int. Cl.
*A61C 7/12* (2006.01)
*A61C 7/16* (2006.01)
(52) U.S. Cl. ......................................................... 433/16
(58) Field of Classification Search ................ 433/8–17, 433/24
See application file for complete search history.

(56) References Cited

U.S. PATENT DOCUMENTS

| | | | | |
|---|---|---|---|---|
| 2,368,851 A * | 2/1945 | Laskin | ............................ | 433/11 |
| 2,379,011 A * | 6/1945 | Laskin | ............................ | 433/16 |
| 3,203,098 A * | 8/1965 | Petraitis | ............................ | 433/23 |
| 3,423,833 A * | 1/1969 | Pearlman | ............................ | 433/16 |
| 3,721,005 A * | 3/1973 | Cohen | ............................ | 433/16 |
| 4,139,945 A * | 2/1979 | DiGiulio | ............................ | 433/16 |
| 4,243,387 A * | 1/1981 | Prins | ............................ | 433/16 |
| 4,353,692 A * | 10/1982 | Karrakussoglu | ............................ | 433/16 |
| 4,597,739 A * | 7/1986 | Rosenberg | ............................ | 433/16 |
| 4,867,678 A * | 9/1989 | Parker | ............................ | 433/8 |
| 5,302,121 A * | 4/1994 | Gagin | ............................ | 433/10 |
| 5,954,502 A * | 9/1999 | Tuenge et al. | ............................ | 433/16 |
| 7,306,458 B1 * | 12/2007 | Lu et al. | ............................ | 433/16 |
| 7,431,586 B1 * | 10/2008 | Silverman | ............................ | 433/9 |
| 2007/0092849 A1 * | 4/2007 | Cosse | ............................ | 433/8 |
| 2007/0259302 A1 * | 11/2007 | Jayawardena | ............................ | 433/10 |
| 2008/0293005 A1 * | 11/2008 | Rahlis et al. | ............................ | 433/16 |
| 2011/0300502 A1 * | 12/2011 | Kishi | ............................ | 433/10 |

* cited by examiner

*Primary Examiner* — Todd Manahan
*Assistant Examiner* — Michael R Ballinger
(74) *Attorney, Agent, or Firm* — Chernoff, Vilhauer, McClung & Stenzel LLP

(57) ABSTRACT

An orthodontic bracket mountable on a tooth for use in retraction mechanics to facilitate movement of teeth along an arch, which includes an archwire-receiving member rotatably mounted on a base and structured to freely rotate when tipping a tooth during sliding of the bracket along an archwire thereby minimizing friction between the archwire and bracket to significantly decrease the required retraction force, and treatment time, thereby minimizing the possibility of root resorption and maintaining the integrity of the root and surrounding bone. A locking mechanism for locking the member against rotation is employed when uprighting the tooth from a tipped position.

3 Claims, 6 Drawing Sheets

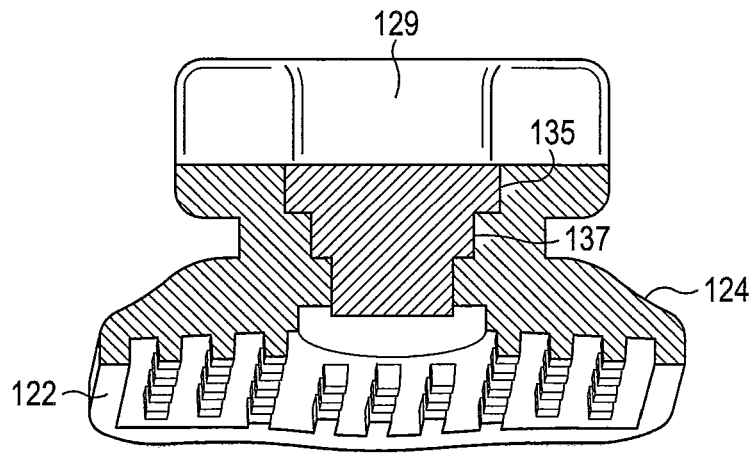
FIG. 3
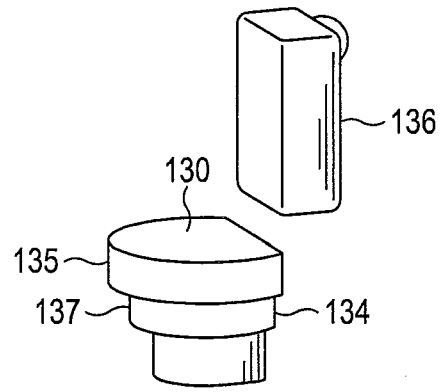
FIG. 4
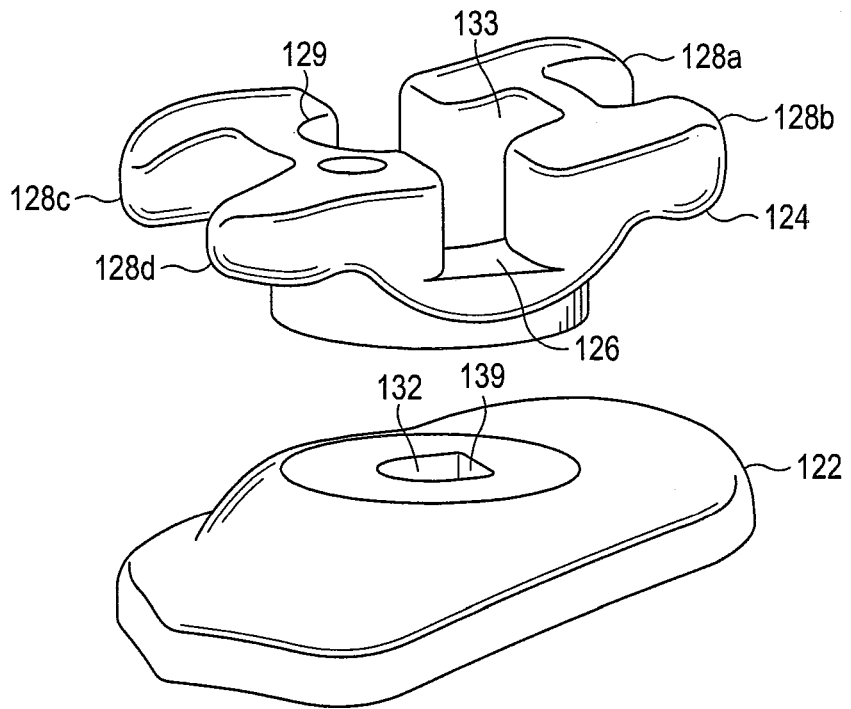

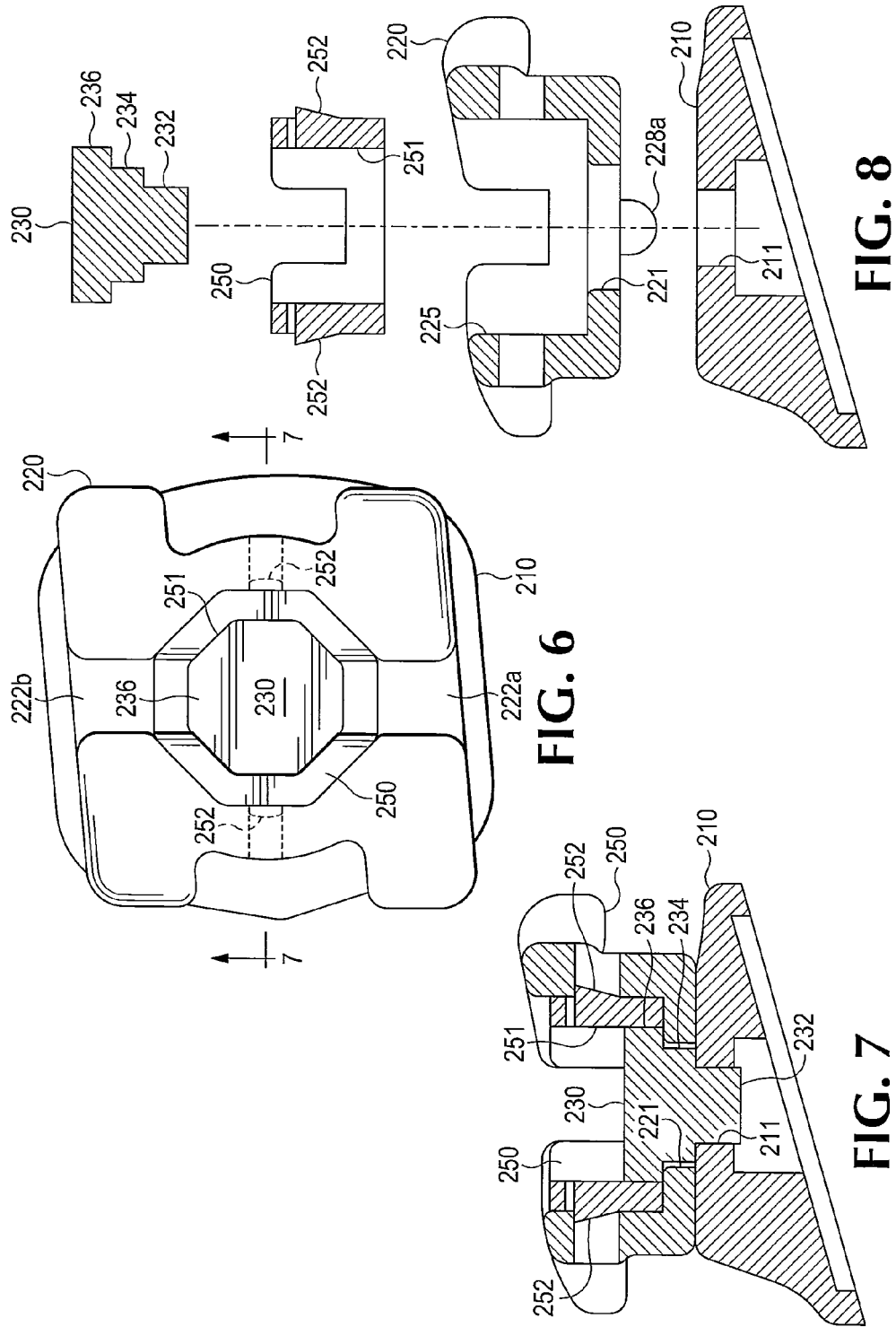

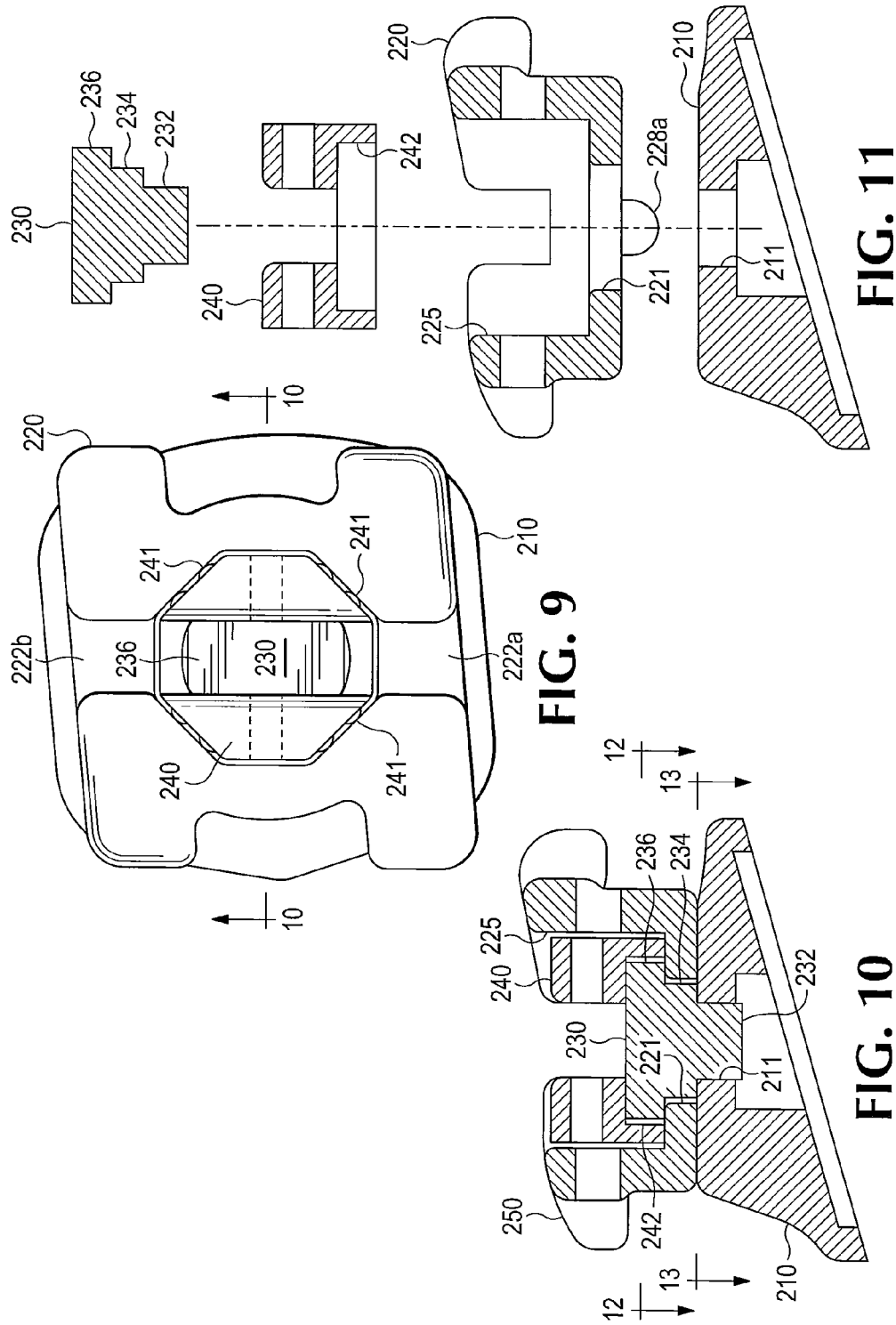

ROTATING ORTHODONTIC BRACKET WITH LOCKING MECHANISM

CROSS-REFERENCE TO RELATED APPLICATIONS

This application is a continuation-in-part of U.S. patent application Ser. No. 13/342,582 filed Jan. 3, 2012, currently pending, which is in turn a continuation-in-part of U.S. patent application Ser. No. 12/807,859 filed Sep. 14, 2010 (now U.S. Pat. No. 8,113,828 issued Feb. 14, 2012).

BACKGROUND OF THE INVENTION

Field of the Invention

This invention relates to a new and improved orthodontic bracket appliance for use in edgewise or straight-wire techniques to facilitate tipping movement of a tooth and sliding of the bracket along an archwire, including structure to minimize frictional resistance, thereby reducing the time of completing the movement to the desired location along the arch, and enhancing the health and comfort of the patient.

BRIEF SUMMARY OF THE INVENTION

The bracket of the present invention includes a rotating archwire-receiving member and a base mountable on a tooth so as to reduce the friction between the archwire and the archwire-receiving member of the bracket. Accordingly, the time of retraction movement of a tooth on which the bracket is mounted to a desired position is significantly shortened. Root resorption is minimized due to the application of light forces, thereby maintaining the integrity of the root and surrounding bone. Accordingly, comfort to the patient is greatly enhanced. This is accomplished in that the bracket includes a base mountable on a tooth and an archwire-receiving member rotatably mounted on the base wherein engageable surfaces between the archwire-receiving member and the base have reduced friction during rotation of the archwire-receiving member on the base member. A unique locking mechanism locks the archwire-receiving member against rotation on the base when the desired movement has been obtained so that forces can be applied to the bracket to direct it to its desired erect position. The archwire-receiving member is rotated so that it is aligned with respect to the tooth and the locking device can be inserted to lock the archwire-receiving member to the base. In this position, the predetermined prescription of the bracket to move the tooth to its ideal position will be achieved. The lock employed is an insert to an archwire-receiving member that locks the member to a rotary axle in such a way that it can no longer turn.

It will be appreciated that the appliance of the invention may be designed with any of the well-known prescriptions utilized in the orthodontic field to obtain the desired final positioning of the teeth on which the appliance is mounted. It may also be made of various materials, such as ceramic, zirconia, plastic or acrylic. Accordingly, in the final stages of treatment, a locking device is inserted to lock the archwire-receiving member to the base. The archwire must first be removed from the archwire slot before rotating and locking the archwire-receiving member to the base. Following insertion of the locking device, the archwire-receiving member cannot rotate relative to the base. Thereafter, the archwire is flexed as needed and reinserted into the slot, and ligated to the archwire-receiving member after which the tooth will be up righted into its ideal position.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 3 is an exploded view of the bracket of FIG. 1.

FIG. 4 is a cut away view of the bracket of FIG. 1 taken along line a-a.

FIG. 6 is a top plan view of an assembled bracket of FIG. 5.

FIG. 7 is a cut-away view along line 7-7 of the bracket of FIG. 6.

FIG. 8 is a cut-away view of the exploded view bracket of FIG. 5.

FIG. 9 is a plan view of the bracket of FIG. 5 including a cover instead of the locking feature.

FIG. 10 is a cut-away view of the bracket of FIG. 9 taken along line 10-10.

FIG. 11 is an exploded cut-away view of the bracket of FIG. 9.

DETAILED DESCRIPTION OF PREFERRED EMBODIMENT

Figure 1:
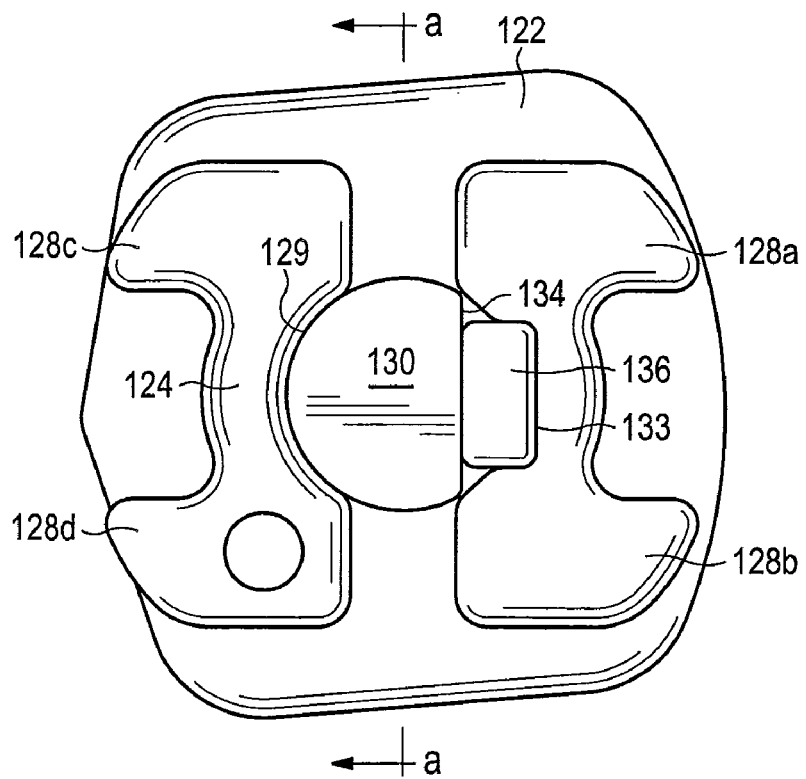
FIG. 1 is a top view of an embodiment of a bracket employing a rotary body and a locking member.
Figure 2:
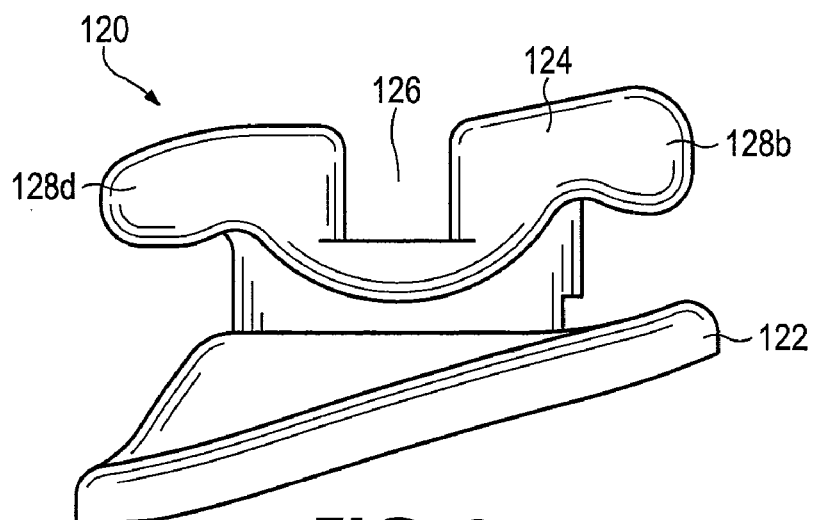
FIG. 2 is a front view of the bracket of FIG. 1.

Referring now to the drawings and particularly to the embodiments of FIGS. 1-13, the orthodontic bracket of the invention includes generally a base and an archwire-receiving member rotatable on the base. An axle coacts with the archwire-receiving member and is suitably anchored in the base for rotatably mounting the archwire-receiving member on the base. It will be appreciated that the base on the archwire-receiving member may be of various shapes and the embodiments of FIGS. 1-13 are primarily illustrative of the invention and the parts of the bracket that produce the rotational mounting of the archwire-receiving member on the base and the ability to employ a locking device for locking the archwire-receiving member to the base during the final stage of treatment. The coacting bearing or sliding surfaces, resulting from rotation of the archwire-receiving member on the base, include means such as bearings to minimize friction between the surfaces so that the archwire-receiving member can freely rotate on the base. It will be appreciated that the bracket may be made of any suitable metal or ceramic.

During the tipping of the tooth and the sliding movement of the tooth and bracket along the archwire, the archwire-receiving member freely rotates on the base so that the bracket can easily slide along the archwire to the predetermined position in which the tooth may then be uprighted. It will be appreciated that suitable force modules, such as springs or elastics, will be employed to cause movement of the tooth and bracket along the archwire. Once the tooth is in the desired position and it is necessary to upright the tooth, the archwire-receiving member is locked to the base so that the archwire can then apply upright forces, as will be more clearly explained below.

A locking device is inserted into the bracket between the archwire-receiving member and the base to engage the archwire-receiving member and lock it to the base when they are aligned with each other.

Referring to FIGS. 1-4, a first embodiment of a bracket is shown. The bracket 120 includes a base 122, which may be affixed to a patient's tooth. A bracket body 124 sits atop the base 120. The body 124 has an archwire slot 126 and tie wings 128a, b, c and d. The body 124 rotates relative to the base on an axle 130 that forms a pivot axis for the body 124. The inner wall shape of the body 124 forms a circular well 129 sized to accommodate the upper part of the axle 130. The upper portion of the axle has stepped arcuate bearing surfaces 135 and 137. The body portion 124 rotates around these portions of the axle 130, which is fixed. The axle 130 is press fitted through a hole in the body 124 into an aperture 132 in the base 122. From the top, the axle 130 is rounded with one side cut away to make a flat side surface 134 in the vertical plane. This provides an anti-rotation feature as will be explained herein. The hole 132 in the base has a flattened side 129 that accepts the axle 130 like a key. Ordinarily the body 124 may rotate atop the base 122 on the axle 130. There is some friction between the upper bearing parts of the axle 135 and 137 and the circular well 129 formed in the bracket body 124, but not enough to prevent free rotation. At some point in the treatment, however, the bracket 120 is locked to prevent rotation. The body portion adjacent tie wings 128a and 128b is shaped with a pocket 133 to accommodate a locking pin 136, which slides into the pocket 133 to contact the flat side 134 of the axle 130 and thus prevent the body 124 from rotating with respect to the base 122. The pin prevents further rotation of the body and hence, of the archwire slot.

Figure 5:
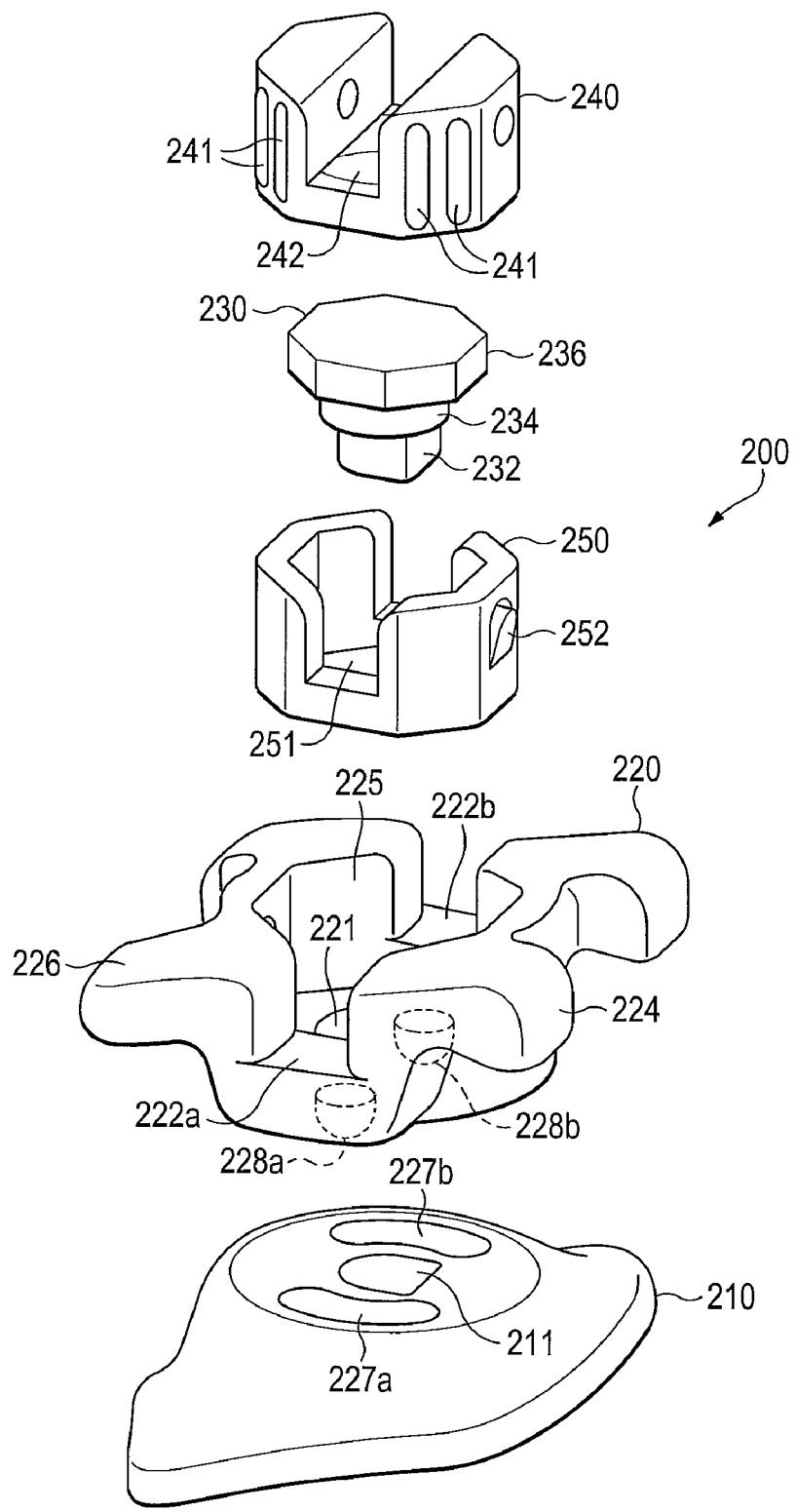
FIG. 5 is an exploded side view of another embodiment of an orthodontic bracket featuring an alternative locking feature.
Figure 12:
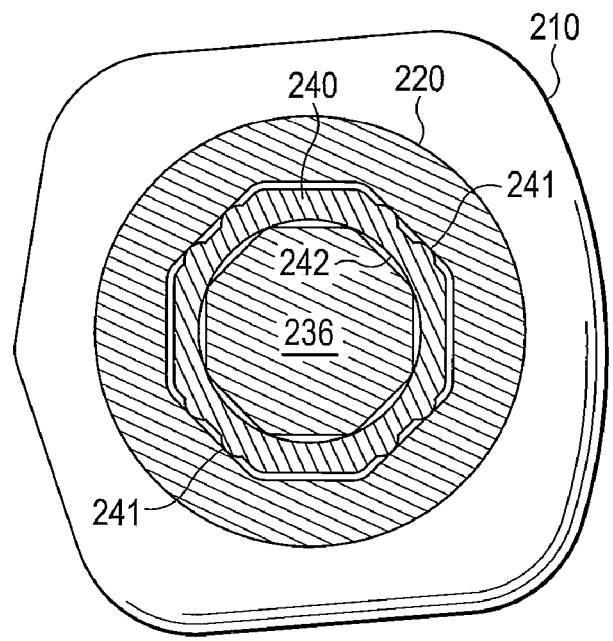
FIG. 12 is a cut-away view of the bracket of FIG. 9 taken along line 12-12 of FIG. 10.
Figure 13:
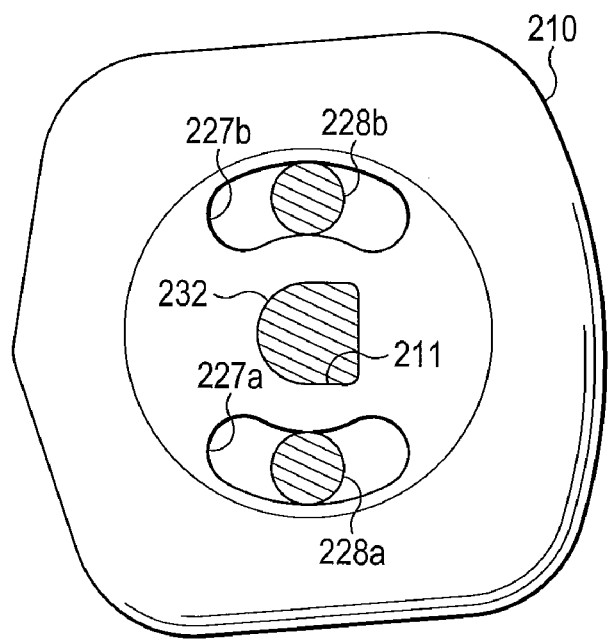
FIG. 13 is a cut-away view of the bracket of FIG. 9 taken along line 13-13 of FIG. 10.

Referring to FIGS. 5-13, another embodiment of a bracket is shown which uses an alternative type of locking mechanism. Referring to FIG. 5, a bracket 200 includes a base 210, which is adapted to be mounted to the surface of a human tooth (not shown). An archwire receiving or body member 220 has chamfered archwire slots 222a and 222b at either distal-mesial end defined by a pair of tie wings 224, 226. The body member 220 is mounted for rotation on the base 210 and has a pair of bearings 228a and 228b that fit into guide channels 227a and 227b on the base, which are arranged as curved arcs. These bearings reduce friction and aid in rotation. In other words, the bearings 228a and 228b in the arcuate channels 227a and 227b are sliding points of contact between the base 210 and body member 220.

The interior walls of the body member 220 form a hexagon. Thus, the interior 225 of the body member 220 has straight sides that intersect to form corners. The particular hexagonal shape is not required, however, and other non-circular shapes such as octagons, squares or other polygonal or even irregular shapes may be used. As will be explained below, the purpose of a non-circular interior 225 in the body member 220 is to provide a keyway function for a corresponding locking member, so virtually any key and keyway shape may suffice for this purpose.

The body member 220 rotates on an axle 230 that is press-fitted into the base 210 through a central aperture 221 in the body member 220. The axle 230 has a distal end 232 with a shaved flat side so as to fit into a correspondingly shaped hole 211 in the base 210 in a key and keyway configuration to prevent rotation of the axle 230. An intermediate cylindrical portion 234 provides a bearing surface for the body member 220. Its central aperture 221 is slightly larger in diameter than the cylindrical portion 234 and provides a modest amount of friction so that the cylindrical portion 234 functions as a bearing, permitting rotation of the body member 220 about the axle. The axle 230 has a head 236 shaped like a hex bolt head. The head 236 occupies part of the interior space of the body member 220 but does not contact its interior walls (shown best in FIG. 6).

The bracket body member 220 is thus permitted to rotate freely in the early stages of treatment and to do so requires only a cover member 240, which fits over the hex head 236. The cover member has a circular bottom opening 242 of a diameter that exceeds the largest outer diameter of the hex head 236 (refer to FIG. 12) and thus rotates over the head 236 as the body member 220 rotates. The cover member 240 has exterior walls which mate with the interior walls of the body member and thus in this example is hexagonally shaped. The cover member 240 also has open ends that compliment the archwire slots 222a and 222b of the body member 220 when inserted over the hex head 236 to permit insertion of an archwire (not shown). In addition, the cover member 240 may be made of a non-metallic material, such as plastic. It may have flutes 241 on its exterior sides that aid in holding it frictionally within the body member 220.

In the later stages of treatment, it is desirous to lock the bracket to prevent the body member 220 from rotating. In such a case, the cover member 240 is removed and the lock spring 250 is inserted. The spring 250 is a hexagonal cylinder whose outer walls fit inside the interior hexagonal walls of the body member 220 and which has an aperture 251 shaped to fit over the hex head 236 of the axle 230 like a socket wrench. The lock spring 250 may have a lateral slot that permits it to be flexed for easy insertion. Once inserted it fits snugly onto the head 236 and inside the body member 220 thus preventing its rotation. The lock spring 250 may also have side tabs 252 that snap into cutouts in the body member 220 to hold the lock spring 250 in position.

It is to be understood that other variations in shape and configuration of the axle and bearings are possible. For example, the axle and the pin could have different shapes or sizes and could fit together in ways different from what is shown. The pin need not be rectangular. It could have any shape as long as its insertion next to the axle would prevent the bracket from rotating. The locking spring and the axle head could also have different shapes, such as square, octagonal, or other polygon or irregular shape. All that is necessary is that the spring bears against the inner walls of the body member and that it fit over the head of the axle so as to prevent rotation.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

The terms and expressions that have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. An orthodontic bracket comprising:
 (a) A base adapted to be affixed to the surface of a patient's tooth,
 (b) An archwire receiving member mounted on said base, said member having interior wall segments, said segments intersecting so as to form corners and a central archwire slot,
 (c) An axle coupling said archwire receiving member to said base so as to permit said archwire receiving member to rotate with respect to said base, said axle having a distal end insertable into said base, a radial bearing portion engaging said archwire receiving member, and a head portion having a polygonal or non-circular shape, and, (d) A selectively removable locking member adapted to fit snugly inside said archwire receiving member and having exterior wall segments conforming to the shape of said interior wall segments and further including an aperture shaped for engaging said head portion so as to lock said archwire receiving member in place to prevent rotation thereof.

2. The bracket of claim 1 further including a selectively removable cover adapted to fit snugly inside said archwire receiving member, said cover having an archwire slot and a bottom aperture for fitting over said head portion of said axle in non-locking fashion.

3. The bracket of claim 1 wherein the head portion has a hexagonal shape and said interior wall segments form a hexagon.

* * * * *